US012318534B2

(12) United States Patent
Bartels et al.

(10) Patent No.: US 12,318,534 B2
(45) Date of Patent: Jun. 3, 2025

(54) MULTILIQUID-NOZZLE (71) Applicant: INVOX BELGIUM NV, Diepenbeek (DE)

(72) Inventors: Frank Bartels, Hattingen (DE); Jürgen Rawert, Cologne (DE)

(73) Assignee: INVOX BELGIUM NV, Diepenbeek (BE)

( * ) Notice: Subject to any disclaimer, the term of this patent is extended or adjusted under 35 U.S.C. 154(b) by 688 days.

(21) Appl. No.: 16/624,220

(22) PCT Filed: Jun. 22, 2018

(86) PCT No.: PCT/EP2018/066714
§ 371 (c)(1),
(2) Date: Dec. 18, 2019

(87) PCT Pub. No.: WO2018/234524
PCT Pub. Date: Dec. 27, 2018

(65) Prior Publication Data
US 2021/0146068 A1 May 20, 2021

Related U.S. Application Data

(60) Provisional application No. 62/523,574, filed on Jun. 22, 2017.

(30) Foreign Application Priority Data

Jun. 22, 2017 (EP) .................... 17177455

(51) Int. Cl.
*A61M 11/06* (2006.01)
*B05B 1/14* (2006.01)
*B05B 1/26* (2006.01)

(52) U.S. Cl.
CPC ............... *A61M 11/06* (2013.01); *B05B 1/14* (2013.01); *B05B 1/26* (2013.01)

(58) Field of Classification Search
CPC . A61M 11/06; B05B 1/14; B05B 1/26; B05B 7/0892; B05B 15/0241; B05B 15/525; B05B 1/083
See application file for complete search history.

(56) References Cited

U.S. PATENT DOCUMENTS 2,785,926 A    3/1957   Lataste
2,933,259 A * 4/1960   Raskin .................... F23D 14/58
                                                                          239/431

(Continued)

FOREIGN PATENT DOCUMENTS

CN        1335783 A    2/2002
CN     104661757 A    5/2005

(Continued)

OTHER PUBLICATIONS

"mechanically." Oxford Languages, Oxford University Press, https://www.google.com/search?rlz=1C1GCEB_enUS804US804&sxsrf=AB5stBhtt8K5rXFCKL8fy7mR2NcB79B9Vg:1689876626761&q=mechanically (Year: 2023).*

*Primary Examiner* — Christopher R Dandridge
(74) *Attorney, Agent, or Firm* — Synergy IP Group AG (57) ABSTRACT

The invention relates to the field of nozzles for inhalation devices for liquids. In particular, the invention relates to a nebulizing nozzle for an inhalation device, suitable for the generation of an aerosol of a medically active liquid, and to inhalation devices comprising such nozzle.
Such nozzle (1) for an inhalation device for medically active liquids (F, F1, F2) for generation of an aerosol has a main axis (Z) and at least three ejection channels (1A, 1B, 1C, 1D) adapted to eject liquid (F, F1, F2) along respective ejection trajectories, wherein at least two collision points (X1, X2)

(Continued)

are provided at which at least two of said ejection trajectories intersect with one another, and/or wherein further, all ejection angles (A, A1, A2) at which the individual trajectories leave the nozzle (1) are identical, or at least one of said ejection angles (A, A1, A2) differs from the other ejection angles (A, A1, A2).

19 Claims, 4 Drawing Sheets

(56) References Cited

U.S. PATENT DOCUMENTS

| | | | | |
|---|---|---|---|---|
| 7,819,342 | B2 * | 10/2010 | Spallek | B05B 11/1084 |
| | | | | 222/137 |
| 8,313,717 | B2 * | 11/2012 | Boe | B05B 1/26 |
| | | | | 423/239.1 |
| 9,089,658 | B2 | 7/2015 | Dunne et al. | |
| 9,259,540 | B2 | 2/2016 | Dunne | |
| 10,105,501 | B2 | 10/2018 | Giroux et al. | |

| | | | |
|---|---|---|---|
| 2003/0075623 | A1 | 4/2003 | Bartels et al. |
| 2012/0055467 | A1 | 3/2012 | Brambilla et al. |
| 2015/0136876 | A1 | 5/2015 | Bartels et al. |

FOREIGN PATENT DOCUMENTS

| | | | | |
|---|---|---|---|---|
| CN | 101918060 | A | | 12/2010 |
| CN | 103079619 | A | | 5/2023 |
| EP | 0 627 230 | | | 2/2000 |
| EP | 1 792 660 | | | 6/2007 |
| GB | 2 466 631 | | | 7/2010 |
| GB | 2536258 | | * | 9/2016 ............ A61M 11/00 |
| GB | 2536268 | | * | 9/2016 ............ A61M 11/00 |
| JP | H08-501979 | A | | 3/1996 |
| JP | 2005046338 | A | | 2/2005 |
| JP | 2006088062 | A | | 4/2006 |
| JP | 2008-540106 | A | | 11/2008 |
| JP | 2015-528745 | A | | 10/2015 |
| RU | 81646 | U1 | | 3/2009 |
| WO | 94/007607 | A1 | | 4/1994 |
| WO | 2006/122561 | A1 | | 11/2006 |
| WO | WO 2009/090084 | A1 | | 7/2009 |
| WO | 2018/234527 | A1 | | 12/2018 |

* cited by examiner

MULTILIQUID-NOZZLE

CROSS-REFERENCE TO RELATED APPLICATIONS

This application is a United States Application under 35 U.S.C. § 371 claiming priority to and the benefit of PCT Application No. PCT/EP2018/066714, filed Jun. 22, 2018, which claims priority to and the benefit of European Application No. 17177455.7, filed on Jun. 22, 2017, and U.S. Provisional Application Ser. No. 62/523,574, filed on Jun. 22, 2017, the contents of each which are hereby incorporated by reference in their entirety.

FIELD OF THE INVENTION

The invention relates to the field of nozzles for inhalation devices for liquids. In particular, the invention relates to a nebulizing nozzle for an inhalation device, suitable for the generation of an aerosol of a medically active liquid.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle. A pumping unit is defined as a unit or device component capable of moving or compressing a fluid material and that comprises at least one pumping chamber, and optionally further comprises auxiliary components as well, such as a body, interfaces, and the like. By means of the pumping unit, the liquid is drawn in a discrete amount, i.e. not continuously, from the reservoir, and fed to the nozzle. The pumping unit works without propellant and generates pressure mechanically.

However, the inhalation device disclosed in said document is usable only for the nebulization of a single type of liquid. In certain situations, it is advantageous if more than one liquid can be atomized simultaneously.

Document U.S. Pat. No. 7,819,342 B2 discloses a setup of an inhalation device which is capable of dispensing two liquids simultaneously. The housing of said inhalation device holds two reservoirs which feed one or two pumping mechanisms. The pressurized liquids are then either dispensed by means of two individual nozzle bodies, so that two separate volumes of atomized liquid are provided. An alternative embodiment discloses an inhalation device with one single nozzle, the nozzle having two ejection channels. The trajectories of said channels intersect, so that a common collision point is provided at which a single volume containing droplets of both liquids is produced.

However, said nozzle is not capable of atomizing more than two liquids at a time. Also, by means of known nozzles which use one collision point, delivering a medically active liquid comprising an active ingredient that, due to its high dose or its low (e.g. aqueous) solubility requires a relatively high volume of liquid to be aerosolized per single dose, is not possible. Also, the nozzle construction needs a fair amount of space which is not always available.

The object of the invention is the provision of a nozzle that avoids the drawbacks of the known art or the provision of a medical aerosol generator comprising such a nozzle. In particular, the nozzle shall be capable of atomizing more than two liquids at a time and consume less space than known solutions.

DESCRIPTION OF THE INVENTION

The object is solved by a medical aerosol generator or inhalation device comprising a nozzle according to claim 1. Advantageous embodiments are described in the dependent claims, the subsequent description, as well as the accompanying figures.

In particular, the invention relates to an aerosol generator for medically active liquids configured and adapted for the generation of an inhalable mist, vapor, or spray, comprising
a) a housing;
b) a reservoir within the housing for holding a medically active liquid;
c) a pumping unit;
d) a nozzle (1);
characterized in that the nozzle (1) has a main axis (Z) and at least three ejection channels (1A, 1B, 1C, 1D) adapted to eject liquid (F, F1, F2) along respective ejection trajectories, wherein at least two collision points (X1, X2) are provided at which at least two of said ejection trajectories intersect with one another, and wherein further, all ejection angles (A, A1, A2) at which the individual trajectories leave the nozzle (1) are identical, or at least one of said ejection angles (A, A1, A2) differs from the other ejection angles (A, A1, A2).

In a preferred embodiment of the invention, the aerosol generator additionally comprises an applicator piece, preferably for oral application. In another preferred embodiment, said applicator piece is a mouthpiece.

In a further preferred embodiment of the invention, the aerosol generator or inhalation device is a handheld device.

Introductorily, some definitions of terms are given which are used throughout the description and claims. The definitions should be used to determine the meaning of the respective expressions unless the context requires a different meaning.

A "medical aerosol generator", "inhaler" or "inhalation device" is a device which is configured and adapted for the generation of an inhalable mist, vapor, or spray. In the context of this invention the terms "medical aerosol generator", "aerosol generator", "inhaler" and "inhalation device" are used interchangeably. In this context, "inhalable" refers to aerosols, mists, vapors or sprays whose properties, including the particle sizes, are such as to render them suitable for administration to a subject. such as a human subject, by inhalation. Inhalable may also be referred to as respirable.

"Atomization" and "nebulization" in the context of inhalers means the generation of fine, inhalable droplets of a liquid. The typical dimensions of atomized droplets are in the range of several microns.

An "aerosol" is a dispersion of a solid or liquid phase in a gas phase. The dispersed phase, also termed the discontinuous phase, is comprised of multiple solid or liquid particles. The aerosol generated by the inhalation device of the invention is a dispersion of a liquid phase in the form of inhalable liquid droplets in a gas phase which is typically air. The dispersed liquid phase may optionally comprise solid particles dispersed in the liquid.

A "liquid" is a fluid material capable of altering its shape to that of a container which holds the liquid but retains a nearly constant volume independent of pressure. A liquid may represent a monophasic liquid solution or a dispersion with a continuous liquid phase and a dispersed phase which may or may not be liquid.

A liquid is "medically active" if it represents, or comprises, a compound or material which has biological or medical activity so that its application is useful for any medical purpose.

A "plurality" means two or more.

A "nozzle" is a unit that serves for the atomization/nebulization of liquid. Generally, the term means the unit in its entirety. However, a nozzle can comprise one or multiple sets of individual, identical or different sub-units. A nozzle may have a plurality of ejection channels for emitting the liquid(s).

The "main axis" of a nozzle is its central axis parallel or collinear to the direction into which the bulk of the emitted aerosol travels after leaving the nozzle.

A "horizontal" plane is a plane that is perpendicular to the main axis.

The "ejection trajectory" is an imaginary and relatively straight line that starts at the end of an ejection channel. It resembles the initial travel path of a liquid emitted from the ejection channel when the inhalation device is operated. It is clear that the nozzle (and the entire inhalation device) must be adapted and configured by means of e.g. a suitable channel geometry and a sufficiently high pressure such that the emitted liquid can be provided in said straight line and with a sharp stream.

Where two or more ejection trajectories intersect, a "collision point" is formed.

A "collision angle" is the angle between the ejection trajectory and the main axis at the collision point. The "ejection angle" is defined as 90 degrees minus the angle ("intermediate angle I") between an ejection trajectory and a line that is parallel to the main axis and intersects with the ejection trajectory. If the collision point is located on the main axis, the parallel line is the main axis itself, and the intermediate angle is the collision angle. If the collision point is not the main axis, the parallel line is offset from the main axis. This "ejection offset" is the distance between the main axis and a collision point measured in a plane perpendicular to the main axis. The ejection angle may also be understood as the angle between an ejection trajectory and a line that is perpendicular to the main axis and connects the exit opening of the ejection channel with the main axis, if the respective collision point is on the main axis; if the respective collision point is not on the main axis, the ejection angle may also be understood as the angle between the ejection trajectory and a line that is perpendicular to the main axis and connects the exit opening of the ejection channel with a line that is parallel to the main axis and intersects with the ejection trajectory.

The terms "upstream" and "downstream" indicate, with respect to the normal flow direction which starts at a reservoir, leads through a pumping unit, followed by the nozzle inlet openings, ejection channels, and exit openings, at which side of a first component a second component is (fluidically) situated. "Upstream" of a first component means that a second component is fluidically arranged before, or in front of, this first component, and "downstream" of a first component means that a second component is fluidically arranged after, or behind, the first component.

Further definitions are given in the subsequent description.

The invention relates in particular to an inhalation device comprising a nozzle. In some embodiments of the invention said inhalation device is a handheld device. In a specific embodiment, the invention relates to a nozzle for a handheld medical aerosol generator.

Said nozzle according to the invention serves for an inhalation device for the generation of an aerosol of medically active liquids, and in particular, of such aerosols which can be inhaled.

The nozzle has a main axis and at least three, and preferably four, ejection channels adapted to eject liquid along respective ejection trajectories, wherein at least two collision points are provided at which at least two of said ejection trajectories intersect with one another.

The main axis is parallel or collinear to the direction along which the aerosol generated from the liquid(s) is emitted from an inhalation device towards a user. The main axis can also be a rotation axis of the nozzle body.

Each of the ejection channels has its own ejection trajectory, i.e. a direction along which the respectively emitted liquid stream leaves its channel. Essentially, the trajectory is a relatively straight line, at least initially, or from the exit opening of the respective ejection channel to the corresponding collision point. It is clear that the parts of said channel which are further away from the exit opening (i.e. inside the nozzle body, or nozzle bulk) can follow directions that are different from said ejection trajectory. It is also clear that liquid which is further away from the nozzle surface will deviate from said straight line, since the impulse is increasingly reduced, and the influence of air resistance and gravity become stronger. The orientation of the latter is primarily defined by the channel orientation directly at the respective exit opening. However, it can also be influenced by the exact shape of the exit opening, as well as deflectors or the like which may optionally be arranged directly behind the exit opening to redirect the emitted fluid.

At least at one of the collision points, at least two of said trajectories intersect, such that a collision-type (or impingement-based) aerosol formation is achieved. Since, according to the invention, at least a third ejection channel is present, said channel can also be directed at said collision point, such that a larger amount of liquid can be atomized. However, in this case, additional channels must be present such that a second collision point is formed, or the third channel can be directed away from said collision point, e.g. against a baffle or the like, such that a second collision point is formed as well.

According to one embodiment, preferably, each ejection trajectory intersects with at least one other ejection trajectory. This means that there is no ejection trajectory which does not intersect with another one, but every ejection trajectory hits at least one other ejection trajectory. In case of four channels, two collision points are present.

According to one embodiment, all ejection angles at which the individual trajectories leave the nozzle are identical with respect to the main axis, and, typically, with respect to the front surface of the nozzle (if essentially flat, and perpendicular to the main axis). If the ejection trajectories lie in a common plane, i.e. in a two-dimensional setup, by using identical angles, more than one collision point can be provided.

According to another embodiment, again with respect to the nozzle's main axis, in a setup where the lateral distances between main axis and channel exit openings are identical, at least one—and preferably at least two—of said ejection angles differ(s) from the others, such that different collision points can be provided. Using the example of a truncated cone, by use of four ejection channels, it is possible to provide a nozzle with two collision points, wherein a first pair of channels provides a first, and a second pair of channels provides a second collision point, one or both being laterally offset from the virtual tip of the truncated cone. In this case, not all the ejection angles are the same with respect to the main axis (e.g. of the truncated cone). Optionally, each of the two ejection trajectories corresponding to the first pair of channels exhibit a first ejection angle, and each of the two ejection trajectories corresponding to the second pair of channels exhibit a second ejection angle, wherein the first ejection angle is different from the second ejection angle. If the exit openings of all channels are positioned symmetrically around the main axis (with the same lateral distance to the main axis), such configuration will result in two collision points, namely a first collision point at the intersection of the two trajectories corresponding to the first pair of channels with the main axis and a second collision point at the intersection of the trajectories corresponding to the second pair of channels with the main axis.

In a two-dimensional setup, preferably, the channels are arranged in a symmetrical manner such that there exists a ("vertical") plane in which the main axis lies which virtually divides the nozzle in two mirroring halves. For each trajectory, the collision angle, which is the angle between the ejection trajectory and the main axis at the collision point, preferably ranges from 15° (sharp angle) to 75° (obtuse angle), and lies more preferably in the range between 30° and 60°; an angle of approximately 45° is also considered to be particularly preferred.

In one embodiment, at least two collision points are provided, wherein each collision point is formed by at least two ejection trajectories having the same ejection angle. Thus, two ejection channels have a first, and two other ejection channels have a second ejection angle differing from the first one.

One advantage of embodiments with a collision point that is fed by more than two ejection channels is that, with regard to this specific collision point, a larger amount of liquid can be nebulized without having to enlarge the cross sections of the individual ejection channels. Thus, the fluidic parameters of each channel can be left untouched, simply by adding additional channels.

An general advantage of a plurality of collision points is that the risk of large droplet formation can possibly be reduced, in particular when larger quantities of liquid are nebulized, because under certain circumstances, a too high concentration of liquid in one location (=collision point) can promote formulation of undesired large droplets. By separating one big collision point into two (or more) smaller collision points, the quantity of liquid required for nebulization at each individual collision point is significantly smaller. In this context, large droplets refer to droplets that are not inhalable or do not reach the lung due to their large size.

Accordingly, the inhalation device of the invention is particularly useful for delivering a medically active liquid comprising an active ingredient that, due to its high dose or its low (e.g. aqueous) solubility requires a relatively high volume of liquid to be aerosolized per single dose, which cannot be delivered by the currently known inhalation devices based on aerosolization by impingement using one collision point.

Also, since a plurality of collision points is provided, each of these can be fed by liquid streams of individual liquids which differ between the collision points. Thus, no mixing of these liquids takes place until the completion of the atomizing phase, which can be advantageous for certain liquids that should not come into contact with each other.

In this respect, the inhalation device of the invention addresses the need for simultaneously delivering, in aerosolized form, two or more active ingredients which are chemically and/or physically not readily compatible.

Since all ejection channels are integrated into one nozzle body, the amount of required space is reduced. Also, the construction easily allows the provision of three or more collision points which can be connected to two or more liquid reservoirs, such that, if desired, three or more liquids can be antomized by the nozzle.

According to another embodiment, along the nozzle's main axis, at least two, or even all collision points are located within the same perpendicular plane, i.e. perpendicular with respect to the main axis. This means that the distance between each collision point and the front surface of the nozzle is essentially the same. This can be advantageous when the individual nebulized liquids (sprays, mists) are approximately of the same size and shall be inhaled as parallel volumes.

In another embodiment, along the nozzle's main axis, at least two or even all collision points are on different perpendicular planes. This means that the distances of at least two collision points with respect to the front surface of the nozzle are different.

If the e.g. two collision points are both located on the main axis, it is possible to produce a central aerosol stream from a first liquid, and a surrounding sheath stream of an aerosol of a second liquid. Such a core-and-sheath stream can advantageously be used for inhalation purposes if e.g. one component of the stream (the sheath) is intended to be dispensed on the trachea, and another (the stream's core) in the bronchioles.

According to another embodiment, with respect to the nozzle's main axis, all collision points are located on the main axis (symmetric setup). This means that, while a plurality of collision points is present, they are located in parallel planes, where the main axis intersects said plane(s). At the same time, when viewed in direction of the main axis, only one collision point is visible.

In another embodiment, at least one collision point is laterally offset from the main axis (asymmetric setup). This means that, when viewed in direction of the main axis, more than one collision point is visible, one or all collision points being laterally displaced from the main axis. The collision points can then lie on different planes, or they can be situated on one common plane.

According to one embodiment, all of the nozzle's ejection channels have the same cross section. Such an embodiment is particularly useful when several liquids of similar physical parameters and in comparable amounts shall be atomized.

In another embodiment, at least one nozzle's ejection channel, or ejection channel pair, has different cross sections than another ejection channel, or ejection channel pair. In other words, the cross sections of individual channels or pairs of channels differ from each other. Such a setup is advantageous when two or more liquids shall be atomized that have differing physical parameters and/or shall be atomized in differing amounts.

With respect to all embodiments described above in which a plurality of collision points is provided, a preferred total number of collision points is two or three, and in particular two. Further, a preferred number of ejection channels is two per collision point.

According to one embodiment, all of the nozzle's ejection channels are (directly or indirectly) in fluid connection with the same liquid reservoir, such that all collision points can be fed with the same liquid. That means that regardless of the number of ejection channels, only one liquid is atomized by the nozzle. Then, preferably, all ejection channels are of the same dimensions, since the type of liquid is the same for all channels.

If the inhalation device has more than one pumping chamber or pumping unit, all pumping chambers or pumping units are connected to the same reservoir, or to reservoirs that hold the same liquid type.

If the inhalation device has just one pumping chamber, it can be fed with the liquid from one or more reservoirs. It then serves as mixing chamber as well, before the liquid is fed to the nozzle.

According to another embodiment, at least two of the nozzle's ejection channels are (directly or indirectly) in fluid connection with individual liquid reservoirs, such that at least one collision point which can be fed with a different liquid (i.e. a second liquid whose composition is different from the first or previously mentioned liquid) is provided. Thus, such a setup is useful for the generation of more than one aerosol at the same time. It is also clear that at least two inlet openings of the nozzle must be connected to individual reservoirs such that at least two different liquids can be atomized.

It should be noted that even when only one liquid composition is to be atomized, an inhalation device having a plurality of reservoirs can be advantageous. The geometry of a reservoir can be standardized. Thus, one inhalation device that receives such standardized reservoirs can be used for the generation of a mixture of individual liquids as well as a "mixture" of the same liquid stemming from a plurality of reservoirs. Further, the mixing ratio of different liquids can easily be adapted simply by using the desired number of reservoirs filled with the individual liquids. For example, if one liquid comprises a medically active agent, and another liquid is a solvent or diluting agent, and the housing holds three reservoirs, a ratio of agent:diluent of 1:1 (one dummy reservoir), 1:2, or 2:1 is possible.

In another embodiment, at least two of the nozzle's ejection channels are connected to a common mixing chamber arranged upstream of the channels and downstream of the respective reservoirs. Herein, a separate volume is provided that is arranged between pumping chamber and nozzle, which has the purpose of mixing liquid from several (yet possibly also identical) sources before feeding them to the ejection channels.

According to one embodiment, at least two ejection channels of the nozzle form a pair (or group, in the case of three or more combined ejection channels) and share a common inlet as well as intersecting trajectories. Preferably, a pair or group of channels consists of two (or three or even more) channels of identical geometry, in order to obtain a most uniform atomizing result. A pair or group generates an aerosol in one collision point. Each pair or group has its own distinct collision point. These distinct collision points may be located at the same or at different horizontal planes.

In another embodiment, all ejection channels of the nozzle have individual inlets. Thus, they do not form pairs, since a pair is characterized by identical liquid flowing through the channels. However, they can still have ejection trajectories that intersect with each other such that a plurality of collision points is provided.

According to one embodiment in which two of the nozzle's ejection channels form a pair, one main feed channel is arranged to connect to the upstream end of the first ejection channel, and a cross channel exists that connects said main feed channel with the upstream end of the second ejection channel. The upstream end of the main feed channel is connected directly or indirectly via a pumping unit to a liquid reservoir. Such a construction is preferably realized in a two-dimensional setup, where all channels are located in the same plane.

The cross channel may have a perpendicular orientation with respect to said main feed channel; thus, the shortest possible fluidic connection is provided. The cross channel can also follow a different path, such as an arched path that might lie in a plane that is perpendicular to the main axis. The cross channel can also be offset to the plane in which the ejection channels of the respective pair are located; however, it is clear that in any case a fluidic connection between the cross channel and the corresponding ejection channels must be provided.

Since the two ejection channels of a pair are arranged on opposite sides with respect to the main axis, and since the cross channel connects the two ejection channels of a pair, only one (common) main feed channel is sufficient for this pair. Thus, only one inlet opening exists which must be coupled to a pumping chamber or reservoir. In this way, a space saving solution is provided with respect to the amount of area that is necessary for connecting one pair of the nozzle to the upstream-arranged component.

In one embodiment of the inhalation device with a nozzle having a plurality of pairs, such as two pairs, the exit openings of the ejection channels of a first pair, with respect to the main axis which then also forms a (rotational) symmetry axis, are in a rotated position relative to the exit openings of the ejection channels of a second pair, e.g. 60° (or another integer factor of 360°), and the respective cross channels are, along said symmetry axis, spaced apart from one another, in order not to intersect with each other. In other words, the aforementioned cross channel construction is repeated for several times, e.g. duplicated or triplicated, and positioned apart from each other by rotating the respective unit comprising a pair of ejection channels, the corresponding cross channel, and the main feed channel around the main axis. If the individual cross channels are arranged on different planes along the main axis, they do not intersect with each other. The result is a turret-like arrangement of inlet openings for the different pairs (and thus, different liquids) which lie on a circular path, placed on the interface between the nozzle body and the component that feeds it with the liquid(s).

According to another embodiment, the nozzle exhibits a front side and a back side opposite to the front side. The front side, which is the face of the device which is oriented towards the user when the device is operated, comprises the exit openings of the ejection channels. The back side, or rear of the nozzle, which faces the interior of the device, is essentially flat and comprises a plurality of openings that form inlets to the main feed channel(s).

Preferably, the device component that connects to the back side of the nozzle is providing a corresponding surface with feed openings, so that each feed opening of said device component connects with an inlet opening of the nozzle. In other words, the interface between nozzle and the component that feeds the nozzle, e.g. the outlet sides of the pumping chambers, is designed such that a simple flat gasket is sufficient. Such a gasket essentially consists of a flat sheet of elastic material with holes at the appropriate positions.

The advantage of such a construction is that the fluid connection can be established safely and easily, and that the cost of providing a seal as well as the interface surfaces is low.

In some embodiments, the nozzle is constructed as a stack of relatively flat plates. Such plates can preferably be fabricated by material subtracting technologies such as etching or the like. Wafers of different materials such as silicon, glass, metal, ceramics, or plastics can form the semi-finished product. The channels are brought into one of the two flat sides of the substrate, or even on both sides. Then, by stacking several of such plates, a nozzle stack providing a plurality of ejection channel pairs can be fabricated.

In other embodiments, the nozzle is constructed from a three-dimensional rotation symmetric basic shape. Such a basic shape can be a (preferably truncated) cone, a cylinder, or a pyramid. Typically, the rotation or symmetry axis of the base shape coincides with the main axis of the finished nozzle.

Subsequently, advantageous combinations of the aforementioned features are provided. These combinations are based on a certain main feature, and can advantageously be combined with the respectively following additional features. A main feature can be combined with one, several, or all of the respective additional features.

For the sake of curtness, instead of repeating descriptions of the respective subsequent features, reference is made to the above description.

According to one embodiment, as a main feature, the nozzle has at least two collision points.

As an advantageous additional feature, at least one of said ejection angles differs from the other ejection angles and/or at least two, or all collision points are located on different planes, and/or at least two of the nozzle's ejection channels are connected to an upstream arranged common mixing chamber, and/or the nozzle is constructed as a stack of two-dimensional plates.

According to another embodiment, as a main feature, the nozzle has at least three ejection channels.

As an advantageous additional feature, at least one of said ejection angles of the nozzle differs from the other ejection angles.

As an advantageous additional feature, the nozzle has at least one collision point is offset from the main axis, and/or at least two, or all collision points are located on different planes, and/or, with respect to the nozzle's main axis, at least one collision point is offset from the main axis, and/or at least one of the nozzle's ejection channels has a different cross section from that of another ejection channel, and/or at least two of the nozzle's ejection channels are connected to individual liquid reservoirs, such that at least one collision point which can be fed with a different liquid is provided, and/or at least two of the nozzle's ejection channels are connected to an upstream arranged common mixing chamber, and/or the nozzle is constructed as a stack of two-dimensional plates.

According to another embodiment, as a main feature, at least two, or all collision points of the nozzle are located on different planes.

As an advantageous additional feature, all of the already described features can be combined with said main feature.

According to another embodiment, as a main feature, with respect to the nozzle's main axis, at least one collision point of the nozzle is offset from the main axis.

As an advantageous additional feature, the nozzle has at least two collision points are provided at which at least two of said ejection trajectories intersect with one another, and/or at least one of said ejection angles differs from the other ejection angles, and/or least two, or all collision points are located on different planes, and/or at least one of the nozzle's ejection channels has a different cross section from that of another ejection channel, and/or the nozzle is constructed from a three-dimensional rotation symmetric basic shape.

According to another embodiment, as a main feature, at least one of the nozzle's ejection channels has a different cross section from that of another ejection channel.

As an advantageous additional feature, at least one of said ejection angles differs from the other ejection angles, and/or least two, or all collision points are located on different planes, and/or at least two of the nozzle's ejection channels are connected to an upstream arranged common mixing chamber, and/or the nozzle is constructed as a stack of two-dimensional plates.

According to another embodiment, as a main feature, at least two of the nozzle's ejection channels are connected to individual liquid reservoirs, such that at least one collision point which can be fed with a different liquid is provided.

As an advantageous additional feature, at least two collision points are provided at which at least two of said ejection trajectories intersect with one another, and/or at least one of said ejection angles differs from the other ejection angles, and/or least two, or all collision points are located on different planes, and/or at least one of the nozzle's ejection channels has a different cross section from that of another ejection channel, and/or at least two of the nozzle's ejection channels are connected to an upstream arranged common mixing chamber, and/or the nozzle is constructed as a stack of two-dimensional plates, and/or the nozzle is constructed from a three-dimensional rotation symmetric basic shape.

According to another embodiment, as a main feature, at least two of the nozzle's ejection channels are connected to an upstream arranged common mixing chamber.

As an advantageous additional feature, at least two collision points are provided at which at least two of said ejection trajectories intersect with one another, and/or at least one of said ejection angles differs from the other ejection angles, and/or least two, or all collision points are located on different planes, and/or at least one of the nozzle's ejection channels has a different cross section from that of another ejection channel, and/or the nozzle is constructed from a three-dimensional rotation symmetric basic shape.

According to another embodiment, as a main feature, the nozzle is constructed as a stack of two-dimensional plates.

As an advantageous additional feature, at least two collision points are provided at which at least two of said ejection trajectories intersect with one another, and/or at least one of said ejection angles differs from the other ejection angles, and/or least two, or all collision points are located on different planes, and/or at least one of the nozzle's ejection channels has a different cross section from that of another ejection channel.

According to another embodiment, as a main feature, the nozzle is constructed from a three-dimensional rotation symmetric basic shape.

As an advantageous additional feature, at least two collision points are provided at which at least two of said ejection trajectories intersect with one another, and/or at least one of said ejection angles differs from the other ejection angles, and/or least two, or all collision points are located on different planes, and/or, with respect to the nozzle's main axis, at least one collision point is offset from the main axis, and/or at least one of the nozzle's ejection channels has a different cross section from that of another ejection channel, and/or at least two of the nozzle's ejection channels are connected to individual liquid reservoirs, such that at least one collision point which can be fed with a different liquid is provided, and/or at least two of the nozzle's ejection channels are connected to an upstream arranged common mixing chamber.

All of the aforesaid combinations of main feature with one, several, or all of the respective additional features result in an advantageous embodiment which requires little space, which is able to deliver a medically active liquid comprising an active ingredient that requires a relatively high volume of liquid to be aerosolized per single dose, and which can nebulize two or more liquids.

All relevant embodiments, options and preferences relating to said nozzle also apply to an inhalation device, inhaler or aerosol generator comprising a nozzle as described above.

Figure 1:
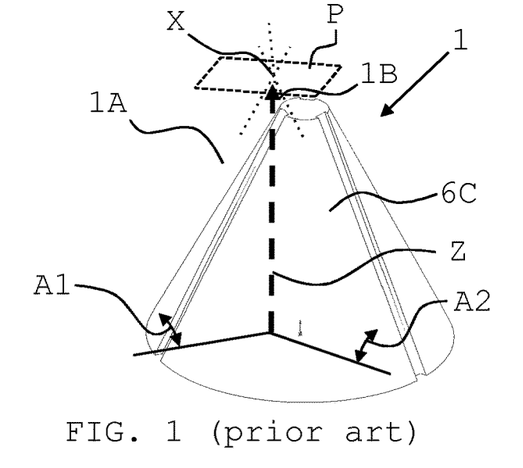
FIG. 1 shows a nozzle according to the prior art.
Figure 2:
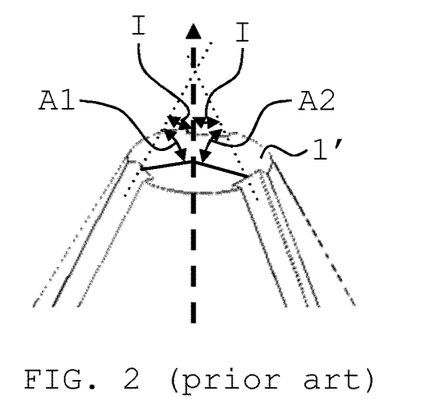
FIG. 2 shows a detail thereof.

In FIG. 1, representing the prior art, a nozzle comprising three ejection channels 1A, 1B, 1C is depicted. The ejection trajectories (dotted lines) intersect in one common collision point X. This collision point is located in plane P having a perpendicular orientation with respect to the main axis Z (this is the common orientation of the plane in which the collision point lies throughout this document, if not stated otherwise). All channels 1A, 1B, 1C are arranged symmetrically and three-dimensionally around main axis Z. The ejection angles (also plotted in FIG. 2 which is a detailed view of the nozzle tip; only angles A1, A2 are shown) as defined herein are identical. The line from which the intermediate angle I is measured is the main axis; thus, the intermediate angle is the collision angle. In this example, all individual trajectories are positioned on the surface of a truncated cone. Since the surface 1' of the truncated cone is parallel to the base circle (no reference numeral), in this example, the angles A1, A2 measured at both locations are identical. Preferably, the channels 1A, 1B, 1C are (laterally) closed with a closure such as a lid (not shown) or the like in a way that liquid (not shown) can pass through the channels, but cannot leave them in undesired (lateral) directions. This can e.g. be achieved in placing the truncated cone inside a cone shaped cap (not shown), the wall(s) of which form(s) a lid for the channels. The channels can be fabricated on the surface of the truncated cone as shown, but also as trenches in the surface of the cap.

Both types may be combined with each other, in that channels are provided alternating in cone and opening, or in that associated half-channels are provided in cone and opening.

Figure 3:
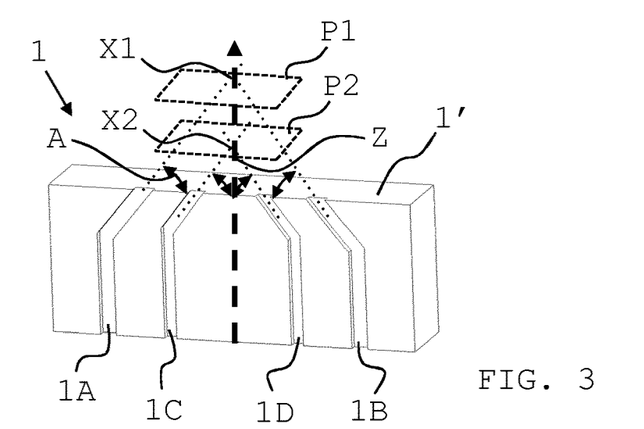
FIG. 3 shows a nozzle according to a first embodiment.

In FIG. 3, a cross sectional view of a nozzle 1 is shown wherein, with respect to the nozzle's 1 main axis Z, again, all ejection angles A are identical (only one reference numeral A plotted); thus, all intermediate angles are the same as well, and they are all measured against the main axis Z. However, the ejection channels 1A-1D lie in a common cross sectional plane (hatching omitted), such that different collision points X1, X2 are provided. These are located in different planes P1, P2 perpendicular to the main axis Z, i.e. collision point X1 and X2 have different distances to the front surface 1' of nozzle 1. At the same time, all collision points X1, X2 are located on main axis Z. Ejection channels 1A and 1B form a first pair, and ejection channels 1C and 1D form a second pair. In this example, nozzle 1 is constructed as/from a "two-dimensional" block.

The present example can be used to produce a central stream (not shown) of an aerosol of a first liquid, and a surrounding sheath stream of an aerosol of a second liquid.

Figure 4:
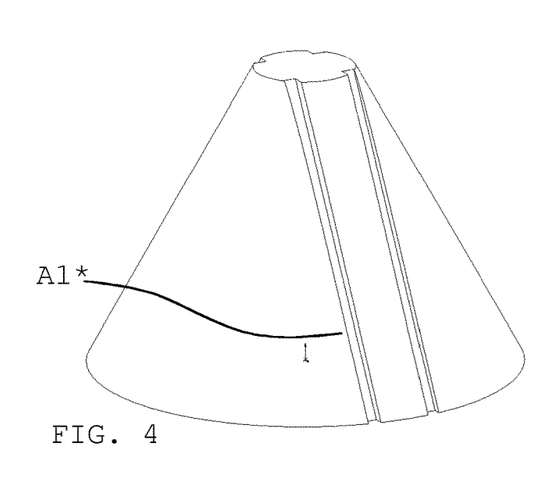
FIG. 4 shows a nozzle according to a second embodiment.
Figure 5:
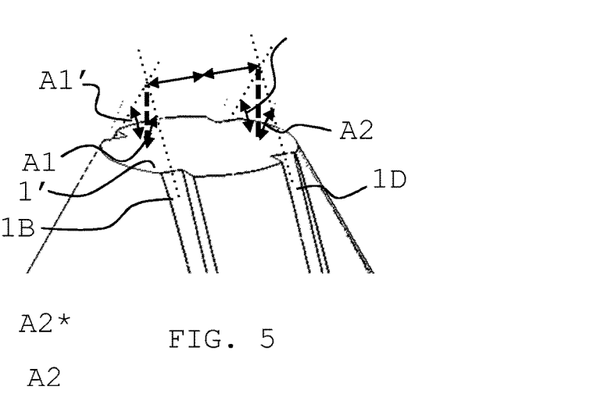
FIG. 5 shows a detail thereof.

In FIG. 4, an embodiment is shown wherein the ejection channels 1A-1D are once again located on the surface of a truncated cone. In this setup, the ejection angles A1, A1' of a first pair of ejection channels 1A, 1B correspond to the ejection angles A2, A2' of a second pair of ejection channels 1C, 1D. However, due to ejection offsets the setup results in two different collision points X1 and X2. FIG. 5 is a detail of the tip of the nozzle. Note that angles A1, A2 in FIG. 4 are the same as in FIG. 5 since the base circle of the cone is parallel to the surface 1' of the truncated cone.

As can be seen in FIG. 4, for example, trajectory of channel 1B is slightly tilted away from the main axis Z in one direction, namely in direction of angle A1", whereas trajectory of channel 1D is tilted in the opposite direction, namely in direction of angle A2". Also, (presently similar) angles A1 and A2 are slightly smaller than angles A1* and A2* which start at the thin dashed lines. These represent lines that start at the base circle of the cone and end at its imaginay tip; channels along the thin dashed lines would have identical angles A1, A2 (and A1', A2', as well as A1", A2") as well, but also result in one common collision point. Therefore, in this example, two pairs of ejection channels 1A, 1B and 1C, 1D are provided, all having identical ejection angles A1, A2, A1' A2' (see FIG. 5), and thus, two collision points X1, X2 are provided, as in the previous example. A lateral ejection offset D exists which is the result of the aforesaid placement of angles. In this embodiment, along the nozzle's main axis Z, all collision points X1, X2 are located within the same plane (not shown) with respect to the nozzle's 1 front surface 1'. At the same time, all collision points X1, X2 a located laterally offset from main axis Z (lateral ejection offset D).

Figure 6:
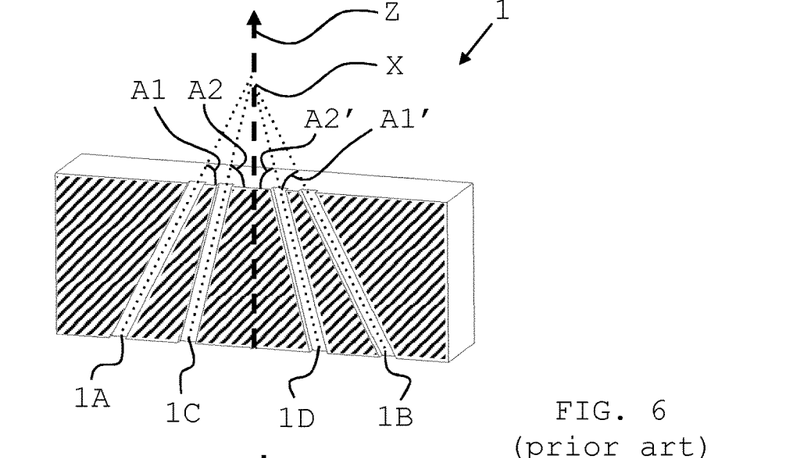
FIG. 6 shows a nozzle according to the prior art.

FIG. 6 depicts a prior art nozzle 1 with four ejection channels 1A-1D whose ejection trajectories have pairwise different ejection angles (A1 and A1' are similar, as well as A2 and A2'), wherein the ejection channels (and the trajectories) lie in a common plane (hatched cross sectional plane). Nozzle 1 is of the "two-dimensional" block-type. The angles A1, A1', A2, A2' are arranged in such a way that all ejection trajectories (dotted lines) intersect in one common collision point X.

Figure 7:
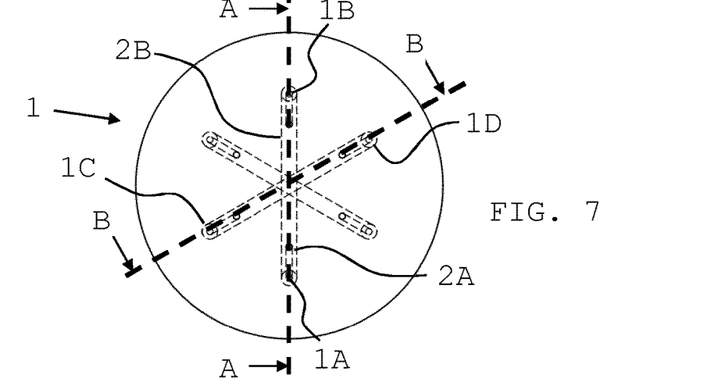
FIG. 7 shows a nozzle according to a third embodiment.

In FIG. 7, a transparent top view on another embodiment of a nozzle 1 is shown. For further details, reference is made to the description of FIGS. 8-11 below which relate to the same embodiment.

Figure 8:
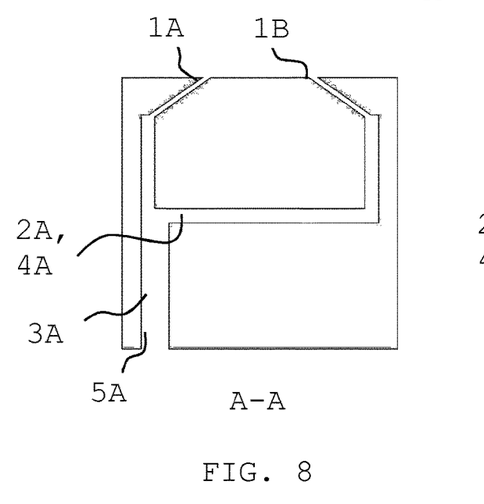
FIGS. 8-10 shows cross sections of a nozzle according to the third embodiment.
Figure 9:
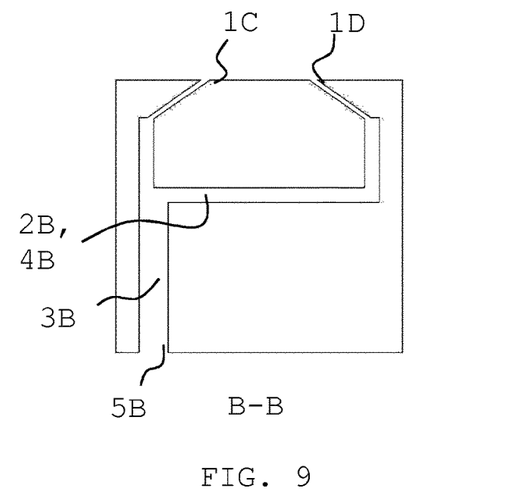

In FIGS. 8 and 9, two cross sections A-A and B-B of nozzle 1 from FIG. 7 are shown (hatching omitted) wherein the ejection channels 1A, 1B and 1C, 1D are connected to an upstream arranged common splitting chamber 2A, 2B. Thus, a separate chamber, or volume, is provided that is arranged between pumping chamber (not shown) and ejection channels 1A, 1B/1C, 1D, which has the purpose of splitting the liquid fed to the nozzle (optionally from several sources) before feeding it to the ejection channels 1A, 1B/1C, 1D.

In the depicted embodiment, two of the nozzle's 1 ejection channels 1A and 1B as well as 1C and 1D form a respective pair, and one main feed channel 3A, 3B is arranged to connect with the beginning of the first ejection channel 1A, 1C and a cross channel 4A, 4B exists that connects said main feed channel 3A, 3B with the end of the respective second ejection channel 1A, 1C. The cross channel 4A, 4B which serves as splitting chamber 2A, 2B runs perpendicular to main feed channel 3A, 3B. Only one respective inlet opening 5A, 5B exists which must be coupled to a pumping chamber or pumping unit (not shown).

In the depicted embodiment, the initially overlapping pairs of ejection channels, with respect to the main axis Z (not shown) which then also forms a symmetry axis, are in rotated positions relative to one another, e.g. by 60° (or another integer factor of 360°), and the respective cross channels 4A, 4B are, along said symmetry axis, spaced apart from one another, in order not to intersect with each other.

Figure 10:
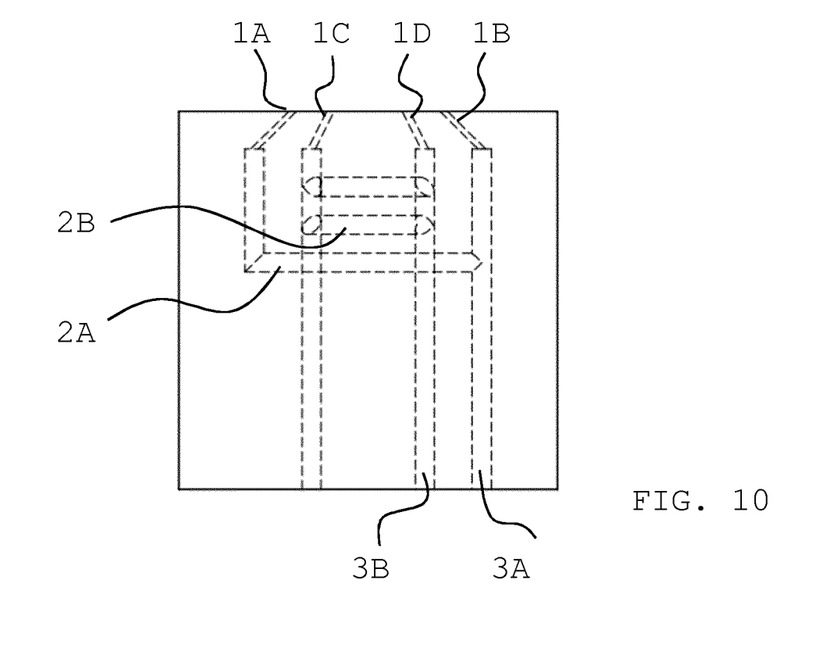

In FIG. 10 which is a transparent side view, a cross section containing hidden lines is depicted, such that all main axially spaced apart cross channels (third cross channel with reference numeral omitted) are well visible. Only two pairs of ejection channels can be seen because of the view direction.

Figure 11:
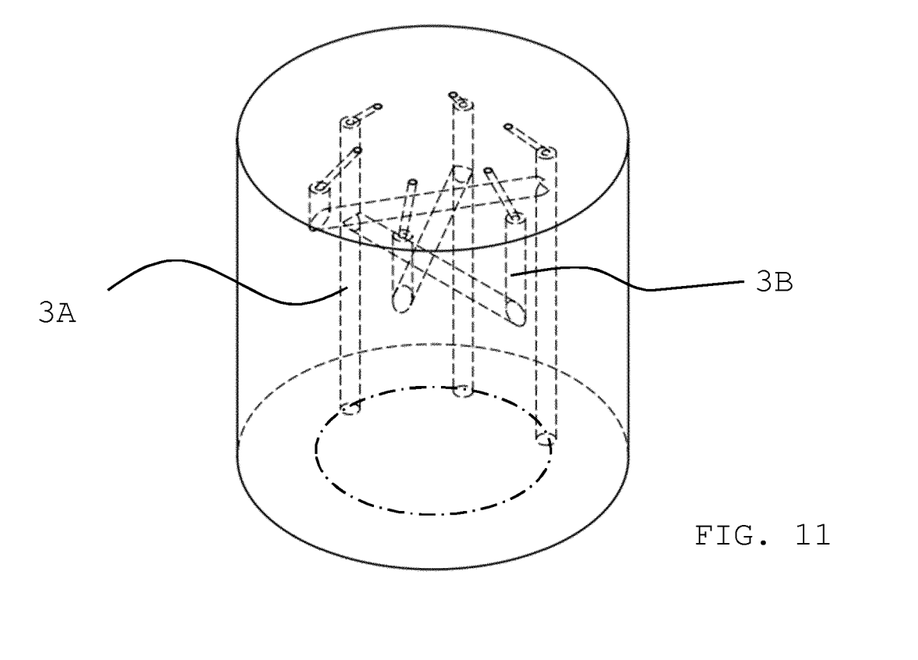
FIG. 11 shows a three-dimensional view of this embodiment.

The aforementioned design can also be seen in FIG. 11 which is a three-dimensional transparent view of nozzle 1 containing the cross sections of FIGS. 8 and 9. By virtually rotating the cross sections, a compact and simple nozzle is obtained whose inlet openings (reference numerals omitted) are located on a circular path (dash-dotted circle). Thus, the respective interface to an upstream arranged component (i.e. pumping chamber, valve section, not depicted) can be designed to be relatively simple.

LIST OF REFERENCES 1 nozzle
1' front surface
1A-1D ejection channels
2A,2B splitting chamber
3,3A,3B main feed channel
4,4A,4B cross channel
5,5A,5B inlet opening
F,F1,F2 liquid
X,X1,X2 collision point
A,A1,A2 ejection angle
A1*, A2*, A1', A2', A1", A2" angle
I intermediate angle
Z main axis
D ejection offset
P,P1,P2 plane

What is claimed is:

1. A nozzle for creating an inhalable from medically active liquid, the nozzle comprising:
   a first 10. A device for generating an inhalable from a medically active liquid, the device comprising:
the nozzle according to claim 1;
a reservoir configured to contain the medically active liquid;
a pumping unit fluidly connected to the reservoir, the pumping unit comprising a pumping chamber configured to receive a discrete portion of the medically active liquid from the reservoir and then pressurize the medically active liquid enclosed within the pumping chamber;
wherein the nozzle is fluidly connected to the pumping unit and is configured to receive the discrete portion of the medically active liquid under pressure and to eject it to generate the inhalable.

11. A device for generating an inhalable from a medically active liquid, the device comprising:
the nozzle according to claim 1;
a first reservoir configured to contain a first liquid;
a second reservoir configured to contain a second liquid;
a pumping unit fluidly connected to the first reservoir and the second reservoir, the pumping unit comprising a pumping chamber configured to receive a discrete portion of the first liquid and a discrete portion of the second liquid forming the medically active liquid and then pressurize the medically active liquid enclosed within the pumping chamber;
wherein the nozzle is fluidly connected to the pumping unit and is configured to receive the discrete portion of the medically active liquid under pressure and to eject it to generate the inhalable.

12. A device for generating an inhalable from medically active liquid, the device comprising:
a nozzle comprising:
a first ejection channel aligned at a first ejection angle from the nozzle, the first ejection channel configured to eject the medically active liquid along a first ejection channel trajectory defined by the first ejection angle;
a second ejection channel aligned at a second ejection angle from the nozzle, the second ejection channel configured to eject the medically active liquid along a second ejection channel trajectory defined by the second ejection angle; and
a third ejection channel aligned at a third ejection angle from the nozzle, the third ejection channel configured to eject the medically active liquid along a third ejection channel trajectory defined by the third ejection angle;
wherein
the first ejection channel trajectory and the second ejection trajectory are aligned to intersect at a first collision point,
the third ejection channel trajectory is aligned to intersect at a second collision point, and
at least the first ejection angle and the second ejection angle are the same relative to a main axis of the nozzle;
a first reservoir configured to contain a first medically active liquid;
a second reservoir configured to contain a second medically active liquid;
a first pumping unit fluidly connected to the first reservoir, the first pumping unit comprising a first pumping chamber configured to receive a discrete portion of the first medically active liquid and then pressurize the first medically active liquid enclosed within the first pumping chamber;
a second pumping unit fluidly connected to the second reservoir, the second pumping unit comprising a second pumping chamber configured to receive a discrete portion of the second medically active liquid and then pressurize the second medically active liquid enclosed within the second pumping chamber;
wherein
the first ejection channel and the second ejection channel are fluidly connected to the first pumping unit and is configured to receive the discrete portion of the first medically active liquid under pressure,
the third ejection channel and the fourth ejection channel are fluidly connected to the second pumping unit and is configured to receive the discrete portion of the second medically active liquid under pressure, and
the nozzle is configured to eject the first medically active liquid at the first collision point and the second medically active liquid at the second collision point, the first medically active liquid and the second medically active liquid forming the inhalable.

13. The nozzle according to claim 12, wherein
the first collision point and the second collision point are within a same plane that is perpendicular to the main axis of the nozzle.

14. The nozzle according to claim 12, wherein
the first collision point and the second collision point are on differing planes that are perpendicular to the main axis of the nozzle.

15. A nozzle for creating an inhalable from medically active liquid, the nozzle comprising:
a first ejection channel aligned at a first ejection angle from the nozzle, the first ejection channel configured to eject the medically active liquid along a first ejection channel trajectory defined by the first ejection angle;
a second ejection channel aligned at a second ejection angle from the nozzle, the second ejection channel configured to eject the medically active liquid along a second ejection channel trajectory defined by the second ejection angle; and
a third ejection channel aligned at a third ejection angle from the nozzle, the third ejection channel configured to eject the medically active liquid along a third ejection channel trajectory defined by the third ejection angle;
a fourth ejection channel aligned at a fourth ejection angle from the nozzle, the fourth ejection channel configured to eject the medically active liquid along a fourth ejection channel trajectory defined by the fourth ejection angle;
wherein
the first ejection channel trajectory and the second ejection trajectory are aligned to intersect at a first collision point,
the third ejection channel trajectory and the fourth ejection trajectory are aligned to intersect at a second collision point,
the first ejection channel and the second ejection channel are fluidly connected to a first inlet via a first cross channel,
the third ejection channel and the fourth ejection channel are fluidly connected to a second inlet via a second cross channel, and
the first cross channel is located in a downstream direction from the second cross channel with the first cross channel and the second cross channel located at non-intersecting positions along the main axis of the nozzle.

16. The nozzle according to claim 15, wherein
the first collision point and the second collision point are within a same plane that is perpendicular to the main axis of the nozzle.
17. The nozzle according to claim 15, wherein
the first collision point and the second collision point are on differing planes that are perpendicular to the main axis of the nozzle.
18. The nozzle according to claim 15, wherein
the first collision point and the second collision point are aligned with the main axis of the nozzle.
19. The nozzle according to claim 15, wherein
one of the first collision point and the second collision point is offset from the main axis of the nozzle.

\* \* \* \* \*

UNITED STATES PATENT AND TRADEMARK OFFICE
CERTIFICATE OF CORRECTION

PATENT NO. : 12,318,534 B2
APPLICATION NO. : 16/624220
DATED : June 3, 2025
INVENTOR(S) : Frank Bartels and Jürgen Rawert Page 1 of 1

It is certified that error appears in the above-identified patent and that said Letters Patent is hereby corrected as shown below:

In the Specification

Column 5, Line 44, 'An general' should be -A general-.

Column 12, Line 25, 'pesently' should be -presently-.

Column 12, Line 29, 'imaginay' should be -imaginary-.

Signed and Sealed this
Twenty-third Day of September, 2025

John A. Squires
*Director of the United States Patent and Trademark Office*